United States Patent [19]

Affeldt et al.

[11] 4,111,057
[45] Sep. 5, 1978

[54] DUAL-INDICATOR MANOMETER FOR AN ELECTROMEDICAL DEVICE

[75] Inventors: Karl-Heinz Affeldt; Gerhard Raupach, both of Berlin, Fed. Rep. of Germany

[73] Assignee: Robert Bosch GmbH, Stuttgart, Fed. Rep. of Germany

[21] Appl. No.: 836,234

[22] Filed: Sep. 23, 1977

[30] Foreign Application Priority Data

Nov. 5, 1976 [DE] Fed. Rep. of Germany ....... 2650627

[51] Int. Cl.$^2$ ............................................... G01L 7/00
[52] U.S. Cl. ...................................... 73/709; 73/729; 128/2.05 G
[58] Field of Search ................. 73/396, 417, 410, 709, 73/729; 128/2.05 G, 2.05 A, 2.05 M; 116/129 N, 129 B, 129 T

[56] References Cited

U.S. PATENT DOCUMENTS

| | | | |
|---|---|---|---|
| 3,117,570 | 1/1964 | Halasz et al. | 128/2.05 M |
| 4,036,061 | 7/1977 | Speidel | 73/396 |

*Primary Examiner*—Donald O. Woodiel
*Attorney, Agent, or Firm*—Spencer & Kaye

[57] ABSTRACT

A dual-indicator manometer for an automatic sphygmomanometer, composed of two pressure indicators each mounted on a shaft and arranged to be individually blocked or released by the armature of an individual electromagnet. Depending on the excitation state of the electromagnet, the armature is raised from or pressed against the surface of the shaft of the associated indicator.

4 Claims, 3 Drawing Figures

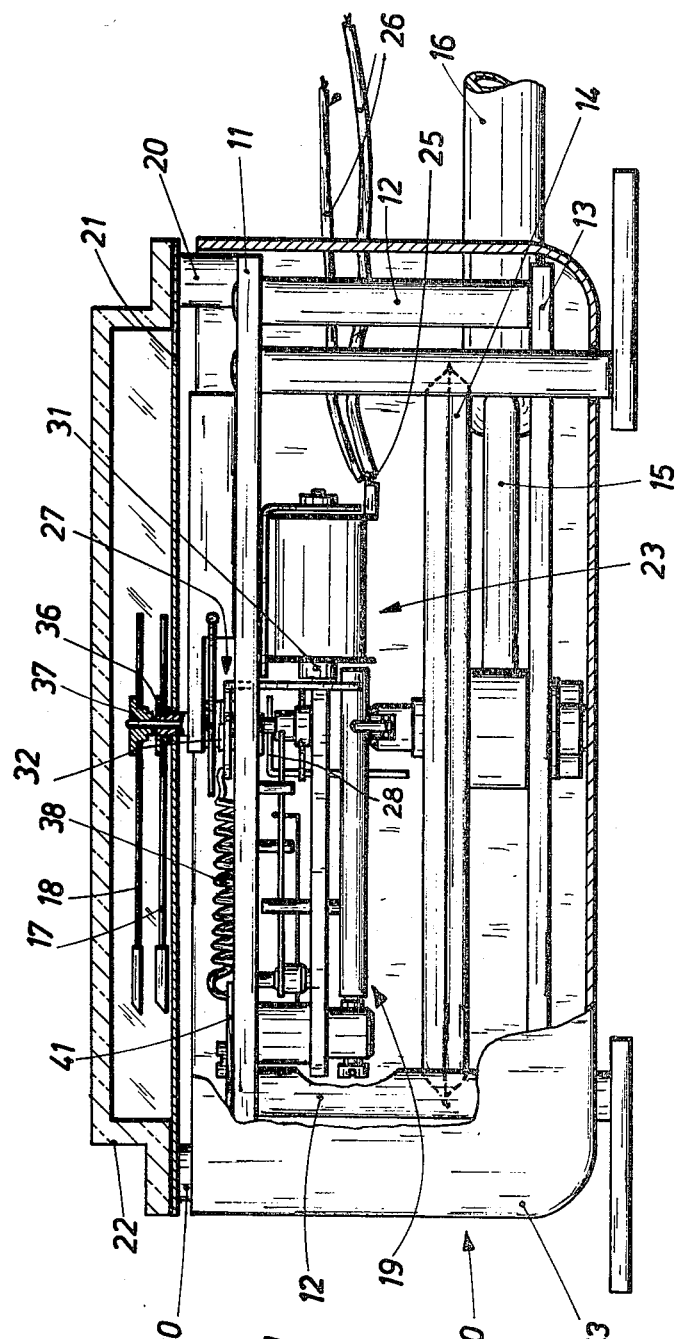
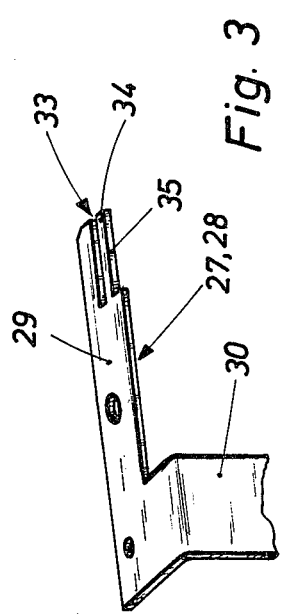

DUAL-INDICATOR MANOMETER FOR AN ELECTROMEDICAL DEVICE

BACKGROUND OF THE INVENTION

The present invention relates to a dual-indicator manometer of the type having two electromagnetically actuable braking members each acting on the shaft of a respective indicator.

A self-recording sphygmomanometer is known which has three indicators, two of which serve to indicate the systolic and diastolic blood pressure values, respectively. This system requires a substantial mechanism to block or release each of the two last mentioned indicators. One such system is disclosed in U.S. Pat. No. 3,056,401, issued to Greenspan et al on Oct. 2, 1962. A particular drawback is that blocking of the indicators cannot be done continuously but can be effected only in dependence on the tooth pitch of a ratchet fastened on each indicator shaft.

SUMMARY OF THE INVENTION

It is an object of the present invention to reduce the number of mechanical elements required for controlling such indicators.

A further object of the invention is to permit blocking of the indicator in any desired indicator position.

These and other objects are achieved by certain improvements in a dual indicator manometer for an electromedical device for measuring and indicating the systolic and diastolic blood pressure values of a patient, which manometer includes two pressure indicators each having a motion transmitting shaft, and two braking members each associated with a respective indicator and including an electromagnet for selectively blocking or releasing the shaft of the respective indicator. The improvements according to the invention reside in that each braking member constitutes an armature associated with its respective electromagnet and movable, in response to the actuation state of the electromagnet, between a blocking position in which the braking member is pressed directly against the surface of the shaft of its associated indicator and a release position in which the braking member is clear of that surface.

According to a particular feature of the invention, the armature of each electromagnet is a two-armed lever which is pivotal about a pin fixed to the manometer housing, one free end of the lever facing the electromagnet and the other free end facing the shaft of the associated indicator.

BRIEF DESCRIPTION OF THE DRAWINGS

FIG. 1 is an elevational cross-sectional view of a dual-indicator manometer constructed according to a preferred embodiment of the invention.

FIG. 3 is a perspective, detail view of an armature of the device of FIGS. 1 and 2.

DESCRIPTION OF THE PREFERRED EMBODIMENTS

Figure 2:
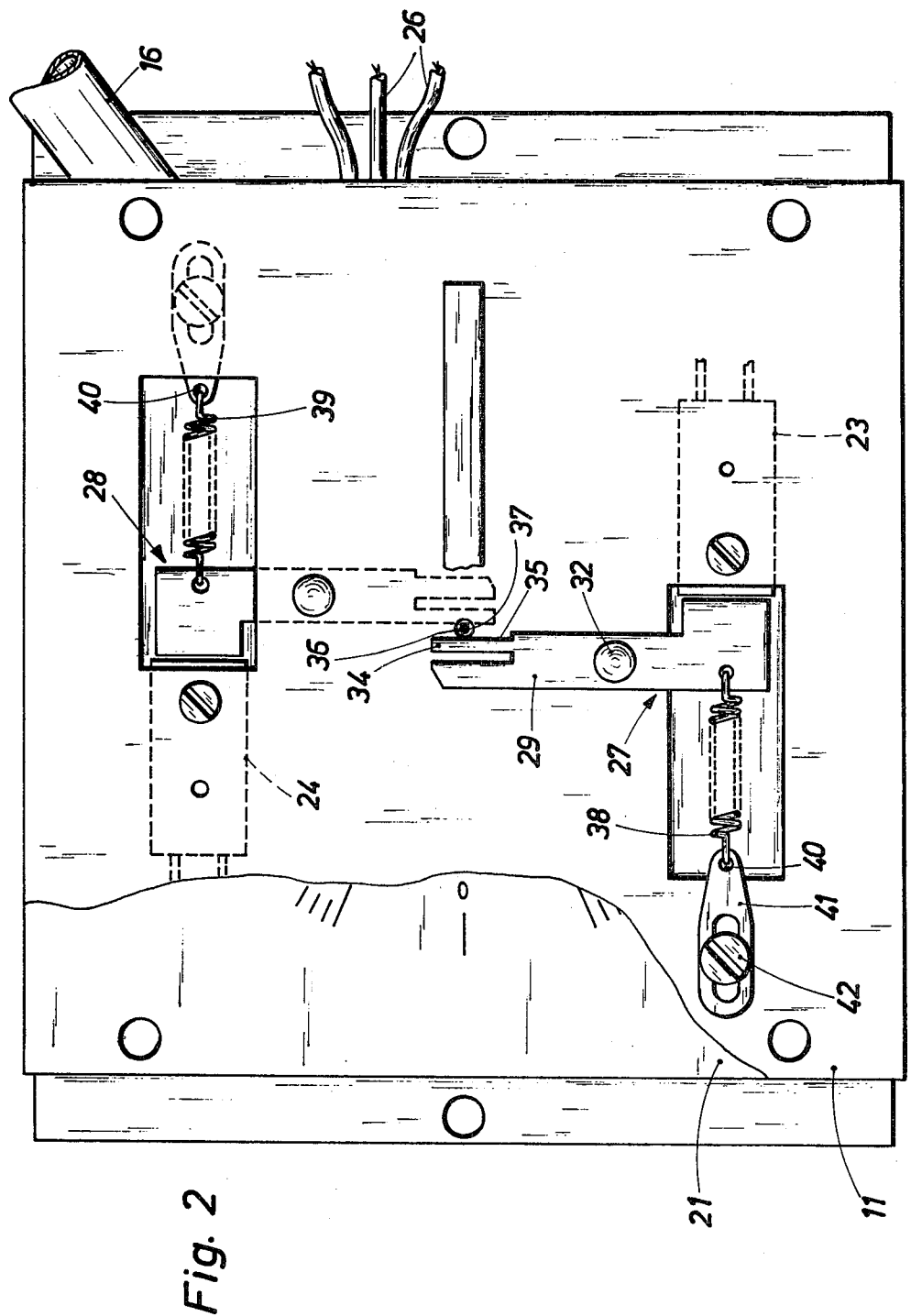
FIG. 2 is a top plan view of the manometer of FIG. 1 with a protective pane shown broken away and the indicator hands removed.

Referring particularly to FIG. 1, there is shown a dual-indicator manometer unit 10 for a blood pressure measuring device. The dual-indicator manometer has a planar, preferably metallic, base plate 11 to which a manometer box, or diaphragm, 14 is fastened by means of holding elements 12 and 13. The manometer diaphragm is provided with a connecting tube 15, while a hose 16 is connected between the free end of tube 16 and the squeeze bulb and pressure cuff of the sphygmomanometer.

A mechanism 19 is provided to transmit the axial expansion and contraction movements of the manometer box 14 to two indicators 17 and 18. This mechanism can be constructed in a manner known to those skilled in the art and will therefore be described only to the extent required for understanding of the present invention.

Above base plate 11, a scale disc 21, partly visible in FIG. 2, is fastened by means of spacers 20 and is covered toward the outside by a transparent protective plate 22 which also covers indicator hands 17 and 18. Two electromagnets 23 and 24 are fastened to the underside of base plate 11, only the first electromagnet 23 being visible in FIG. 1. Each electromagnet has two electric terminals 25 which are connected to electric conductors 26.

Each of the identically designed electromagnets 23 and 24 is provided with an armature 27 or 28 having the form shown in FIG. 3. Each armature is constituted by a strip-shaped sheet metal piece 29 having a flap 30 bent at approximately a right angle to the main part of the piece and located adjacent a core 31 of the electromagnet, as best seen in FIG. 1.

Each armature 27 and 28 is designed as a two-armed lever which is pivotal about a respective bearing pin 32 fastened in base plate 11. One free end of each lever carries its respective flap 30 and the other free end is divided by a longitudinal slit 33, shown in FIG. 3, so as to produce a rod-shaped braking member 34 having a braking surface 35.

While the braking surface of armature 27 faces a hollow shaft 36 bearing the first indicator hand 17, the braking surface of armature 28 of the second electromagnet 24 faces the shaft 37 of the second indicator hand 18. Each braking element is made in the form of a rod so that it can be bent during installation of the manometer to provide sufficient clearance between its surface 35 and the associated hollow shaft 36 or shaft 37, respectively, when the electromagnet 23 or 24 is excited.

Each armature 27 or 28 has its one free end connected to a respective tension spring 38 or 39 to urge the associated armature in a direction which causes the braking surface 35 to bear against shaft 36 or 37.

In the operating state depicted in FIG. 1, the electromagnets are deactuated and tension springs 38 and 39 force braking surfaces 35 firmly against hollow shaft 36 and shaft 37, respectively, to thus block the indicators. The braking force required for the blocking action can be made adjustable by inserting one end of each tension spring in an opening 40 in a respective plate 41 which is displaceably mounted on base plate 11 and fixed in the desired position by means of a screw 42.

The parts of the dual-indicator manometer 10 disposed below scale plate 21 are protected by a housing 43 which is provided with openings for the passage of hose 16 and the electrical lines 26. An electrically insulating plastic is preferred as the material for housing 43.

The illustrated dual-indicator manometer operates as follows. If the blood pressure of a patient is to be measured, current must initially be switched on to excite both electromagnets 23 and 24. This attracts the armatures 27 and 28 in opposition to the force of tension springs 38 and 39 and lifts the braking members 34 away from the hollow shaft 36 of the first indicator hand 17 and the shaft 37 of the second indicator hand 18.

If now the pressure cuff which has been placed about the arm of the patient is pumped up by means of a squeeze bulb, the air pressure is simultaneously transmitted to the manometer diaphragm 14 to cause it to expand in the axial direction. Corresponding with this expansion, both indicator hands are moved simultaneously so that the increasing pressure in the pressure cuff can be read off on the scale of plate 21. The cuff pressure is now increased until a pressure value has been reached which lies above the systolic pressure normally to be expected for the patient.

If now the actual measuring process is initiated, for example by pressure on a key or button, the compressed air contained in the pressure cuff is caused to escape slowly through a valve so that the indicated pressure drops continuously.

At a certain cuff pressure the so-called Korotkov noises start which are evaluated, for example, in an evaluation and control device including a microphone. With the onset of the Korotkov noises, delivery of current to the first electromagnet 23 is terminated and thus the first indicator hand 17 becomes blocked. This indicator then indicates the systolic pressure of the patient.

While the first electromagnet continues to receive no current, the second electromagnet 24 is excited for short intervals with every Korotkov noise so that the second indicator 18 can adjust itself to the instantaneous cuff pressure, which drops slightly between two successive Korotkov noises. After each Korotkov noise the second indicator is blocked in that delivery of current to the associated electromagnet 24 is terminated. After the last Korotkov noise the second indicator then indicates the diastolic blood pressure.

When the preferably automatic, measuring process is completed, the electromagnets remain deenergized. The indication of the pressure values remains unchanged until the beginning of a new measurement, when the indicators are released by excitation of the two electromagnets.

It will be understood that the above description of the present invention is susceptible to various modifications, changes and adaptations, and the same are intended to be comprehended within the meaning and range of equivalents of the appended claims.

What is claimed is:

1. In a dual indicator manometer for an electromedical device for measuring and indicating the systolic and diastolic blood pressure values of a patient, which manometer includes two pressure indicators, each having a motion transmitting shaft, and two braking members each associated with a respective indicator and including an electromagnet for controlling movement of its respective indicator for selectively blocking or releasing the shaft of the respective indicator, the improvement wherein each said braking member constitutes an armature associated with its respective electromagnet and having the form of a two-armed lever which is pivotal about a fixed axis, with one free end of said lever facing its associated electromagnet and the other free end of said lever facing its associated shaft, each said lever being pivotally movable, in response to the actuation state of said electromagnet, between a blocking position in which said braking member is pressed directly against the surface of said shaft of its associated indicator and a release position in which said braking member is clear of that surface.

2. An arrangement as defined in claim 1 further comprising spring means connected to said one free end of each of said levers for forcing each said lever into its blocking position when its associated electromagnet is deactuated.

3. An arrangement as defined in claim 2 wherein each said two-armed lever is formed of a narrow strip of sheet metal whose free end facing said shaft of the associated indicator is slotted in the longitudinal direction of said sheet metal strip.

4. An arrangement as defined in claim 1 wherein each said two-armed lever is formed of a narrow strip of sheet metal whose free end facing said shaft of the associated indicator is slotted in the longitudinal direction of said sheet metal strip.

* * * * *